US010529447B2

(12) United States Patent
Dorn

(10) Patent No.: US 10,529,447 B2
(45) Date of Patent: Jan. 7, 2020

(54) DETERMINING AN ANONYMIZED DOSE REPORT IMAGE

(71) Applicant: Siemens Healthcare GmbH, Erlangen (DE)

(72) Inventor: Karlheinz Dorn, Kalchreuth (DE)

(73) Assignee: SIEMENS HEALTHCARE GMBH, Erlangen (DE)

( * ) Notice: Subject to any disclaimer, the term of this patent is extended or adjusted under 35 U.S.C. 154(b) by 14 days.

(21) Appl. No.: 15/988,266

(22) Filed: May 24, 2018

(65) Prior Publication Data

US 2018/0350454 A1 Dec. 6, 2018

(30) Foreign Application Priority Data

May 30, 2017 (EP) ..................... 17173349

(51) Int. Cl.
*G16H 10/60* (2018.01)
*G06F 19/00* (2018.01)
(Continued)

(52) U.S. Cl.
CPC ............. *G16H 10/60* (2018.01); *A61B 6/461* (2013.01); *A61B 6/5294* (2013.01); *G06F 19/321* (2013.01); *G16H 15/00* (2018.01)

(58) Field of Classification Search
CPC ...... A61J 2205/70; A61J 7/0418; A61J 7/049; A61J 1/00
(Continued)

(56) References Cited

U.S. PATENT DOCUMENTS 7,440,817 B2 * 10/2008 Fu ........................ G16H 40/63
700/237
8,521,323 B2 * 8/2013 Imai ........................ B25J 11/00
141/104
(Continued)

FOREIGN PATENT DOCUMENTS

CN 103971061 A 8/2014
CN 104137129 A 11/2014
(Continued)

OTHER PUBLICATIONS

Borovikov, Eugene: "A survey of modem optical character recognition techniques"; 2014; https://arxiv.org/abs/1412.4183v1.
(Continued)

*Primary Examiner* — Yosef Kassa
(74) *Attorney, Agent, or Firm* — Harness, Dickey & Pierce, P.L.C.

(57) ABSTRACT

In a method, a personal dose report image is received via a first interface. The personal dose report image includes personal data and dose data of an imaging by way of ionizing radiation. The personal data and the dose data are contained as rasterized text in the personal dose report image and the personal data or the dose data includes a first signal word. A first position of the first signal word in the personal dose report image is determined through optical character recognition. An image area in the personal dose report image is determined based on the first position, the image area including at least a part of the personal data. An anonymized dose report image based on the personal dose report image is determined, at least the image area of the anonymized dose report image corresponding to the image area of the personal dose report image being anonymized.

17 Claims, 7 Drawing Sheets

(51) Int. Cl.
*G16H 15/00* (2018.01)
*A61B 6/00* (2006.01)

(58) Field of Classification Search
USPC ........ 382/128, 130, 170, 209, 278; 700/223, 700/236; 128/922, 923
See application file for complete search history.

(56) References Cited

U.S. PATENT DOCUMENTS

| | | | |
|---|---|---|---|
| 8,694,646 B1 | 4/2014 | Kothari | |
| 8,763,553 B1 * | 7/2014 | Shannehan | A61J 7/04 116/308 |
| 8,896,428 B2 * | 11/2014 | Shalala | B65B 7/28 340/309.16 |
| 2006/0124501 A1 * | 6/2006 | McNeely | A61J 7/04 206/534 |
| 2008/0056556 A1 * | 3/2008 | Eller | G06F 19/3462 382/142 |
| 2011/0184753 A1 * | 7/2011 | Tripoli | G06Q 10/00 705/2 |
| 2014/0372149 A1 | 12/2014 | Friese et al. | |
| 2015/0128285 A1 | 5/2015 | Lafever | |
| 2017/0177570 A1 | 6/2017 | Dorn | |

FOREIGN PATENT DOCUMENTS

| | | |
|---|---|---|
| DE | 102015225735 A1 | 6/2017 |
| EP | 1605348 A2 | 12/2005 |

OTHER PUBLICATIONS

Extended European Search Report #17173349.6 dated Nov. 24, 2017.
European Office Action and English translation thereof dated Apr. 18, 2018.
European Office Action and English translation thereof dated May 23, 2018.
European Office Action and English translation thereof dated Aug. 3, 2018.
European Intent to Grant and English translation thereof dated Jan. 3, 2019.
Chinese Office Action and English translation thereof dated Sep. 4, 2019.

* cited by examiner

FIG 3

| | Rad. Univ. Clinic Anytown | | | | Aquillion ONE | |
|---|---|---|---|---|---|---|

Study Date:          2015/06/25
Dose Display:        IEC 3.0
Total DLP(myGy.cm):       (Head):  -    (Body): 625.70

1. Thorax Routine

| No. | Protocol | #of scan(s) | KVP | CTDivol | DLP |
|---|---|---|---|---|---|
| 1 | Dual Scano | 1 | 120 | | |
| 2 | Dual Scano | 1 | 120 | | |
| 3 | S&V | 1 | 120 | 3.90(Body) | 3.10(Body) |
| 4 | Sure Start | 1 | 120 | 136.30(Body) | 27.30(Body) |
| 5 | GG-Hel | 1 | 120 | 13.30(Body) | 595.30(Body) |

Patient ID :            1968.06.16
Age :                   47Y
Sex :                   Man SUREXposure

| No. | Name | SD | SureIQ Name | Image Thickness | Recon-FC | ⌀DS | XY |
|---|---|---|---|---|---|---|---|
| 5 | Thorax | 15.00 | Body-Std-Axial | 3.0 | FC18 | Standard | 3D |

| Rad. Univ. Clinic Anytown | | | | Aquillion ONE | |
|---|---|---|---|---|---|
| Study Date: | 2015/06/25 | | | | |
| Dose Display: | IEC 3.0 | | | | |
| Total DLP(myGy.cm): | (Head): — | | (Body): 625.70 | | |

1. Thorax Routine

| No. | Protocol | #of scan(s) | KVP | CTDivol | DLP |
|---|---|---|---|---|---|
| 1 | Dual Scano | 1 | 120 | | |
| 2 | Dual Scano | 1 | 120 | | |
| 3 | S&V | 1 | 120 | 3.90(Body) | 3.10(Body) |
| 4 | Sure Start | 1 | 120 | 136.30(Body) | 27.30(Body) |
| 5 | GG-Hel | 1 | 120 | 13.30(Body) | 595.30(Body) |

SUREXposure

| No. | Name | SD | SureIQ Name | Image Thickness | Recon-FC | ⌀DS | XY |
|---|---|---|---|---|---|---|---|
| 5 | Thorax | 15.00 | Body.Std.Axial | 3.0 | FC18 | Standard | 3D |

1/1

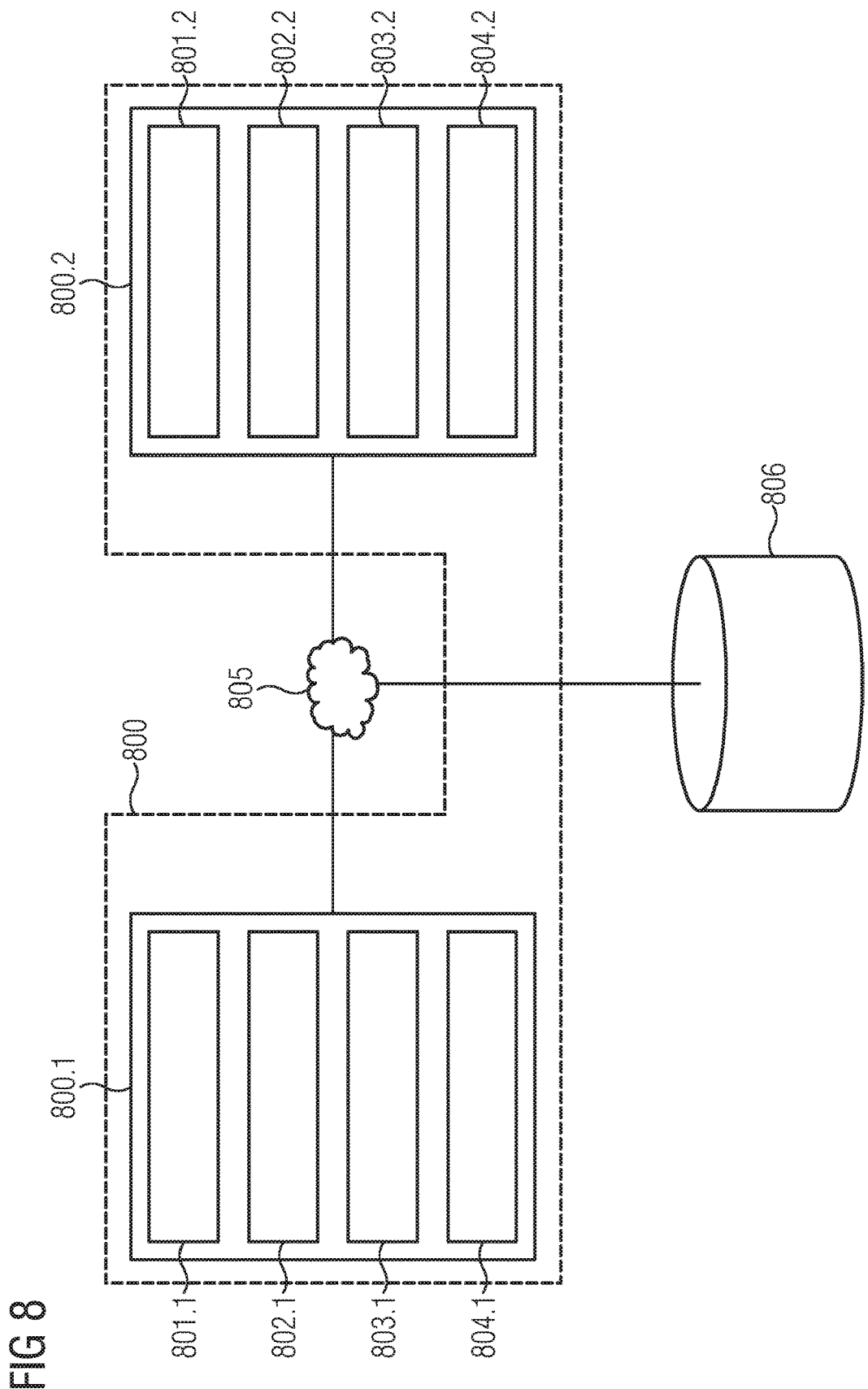

DETERMINING AN ANONYMIZED DOSE REPORT IMAGE

PRIORITY STATEMENT

The present application hereby claims priority under 35 U.S.C. § 119 to European patent application number EP17173349.6 filed May 30, 2017, the entire contents of which are hereby incorporated herein by reference.

FIELD

At least one embodiment of the present invention is directed to a method of determining an anonymized dose report image.

BACKGROUND

In medical imaging examinations, by way of ionizing rays, in particular with x-rays, monitoring and evaluation of the radiation dose taken up by the patient is usual and in some cases is a legislative requirement. A medical imaging examination by way of ionizing radiation can involve an x-ray recording or a computed tomography imaging for example.

Since information processing systems for image data from medical examinations, although they can read image data, cannot however always read it with metadata of any given formats, an expanded process is needed for storing metadata about an examination as rasterized text in a dose report image, and for making the dose report image available. Metadata can in particular involve personal data of the examined patient (for example name, age, date of birth, address and/or sex) as well as dose data of the examination, for example a CTDI (Computed Tomography Dose Index), the WED (Water-Equivalent Diameter) or the DLP (Dose Length Product). The name dose information image is also known as a synonym for dose report image.

For efficient monitoring and evaluation of the dose data it is desirable to store these dose report images centrally, in particular also with a third-party provider for storage services (a so-called cloud storage provider). However for this the personal data must be removed from the dose report image or said data must be anonymized, in order to satisfy legislative requirements for data protection.

For this it is known that individual personal data can be localized via optical character recognition (abbreviated to OCR) and anonymized on the basis of its position. However, because of the variability of the personal data characters, recognition is difficult, for example a name of a person can be not in widespread use or can contain characters from other character sets (umlauts, accents, Arabic or Chinese fonts). Furthermore, with such a method it cannot be excluded that personal data continues to be present in the anonymized dose report image.

Furthermore the processing of dose report images based on a positive list is known from the German patent with the file reference DE 10 2015 225 735.5. Here dose report images are transmitted if the information contained therein can be extracted via text recognition, and the corresponding medical imaging device is transmitted to a positive list. It is not disclosed here however how personal data can be anonymized in the dose report images.

SUMMARY

At least one embodiment of the present invention is provides a method for providing an anonymized dose report image without personal data quickly and reliably.

Embodiments of the present invention is directed to a method for providing an anonymized dose report image, a determination unit, a computer program product, and also a computer-readable storage medium.

Features, advantages or alternate forms of embodiment mentioned here are likewise also to be transferred to the other claimed subject matter and vice versa. In other words the physical claims (which are directed to a device for example) can also be developed with the features that are described or claimed in conjunction with a method. Corresponding physical modules embody the corresponding functional features of the method here.

At least one embodiment of the present invention is direct to a method for providing an anonymized dose report image. In at least one embodiment of the method, a personal dose report image is received via a first interface, wherein the personal dose report image comprises personal data and dose data of an imaging via ionizing radiation, wherein the personal data and the dose data is contained as rasterized text in the personal dose report image and wherein the personal data or the dose data includes a first signal word. Furthermore a first position of the first signal word in the personal dose report image is determined by optical character recognition via a first computing unit. Furthermore an image area in the personal dose report image is determined based on the first position via the first computing unit, wherein the image area comprises at least a part of the personal data. Furthermore an anonymized dose report image based on the personal dose report image is determined via the first computing unit, wherein at least the image area of the anonymized dose report image corresponding to the image area of the personal dose report image is anonymized. In particular the part of the personal data comprised by the image area, as well as the first signal word, can contain further personal data, in other words the part of the personal data comprised by the image area does not exclusively contain the first signal word.

At least one embodiment of the invention further relates to a determination unit for determining an anonymized dose report image, comprising:

First interface, embodied for receiving a personal dose report image,
wherein the personal dose report image comprises personal data and dose data of an imaging by way of ionizing radiation, wherein the personal data and the dose data are contained as rasterized text in the personal dose report image, and wherein the personal data or the dose data comprise a first signal word, First computing unit, embodied for first determination of a first position of the first signal word in the personal dose report image by optical character recognition,
further embodied for second determination of an image area in the personal dose report image based on the first position, wherein the image area comprises at least a part of the personal data,
further embodied for third determination of an anonymized dose report image based on the personal dose report image, wherein at least the image area of the anonymized dose report image corresponding to the image area of the personal dose report image is anonymized.

At least one embodiment of the invention also relates to a computer program product with a computer program as well as to a non-transitory computer-readable storage medium. A largely software-based realization has the advantage that determination units also used previously can be upgraded in a simple manner by a software update, in order to work in the inventive way. Such a computer program product, in addition to the computer program, can if necessary comprise additional elements such as e.g. documentation and/or additional components, as well as hardware components, such as e.g. hardware keys (dongles etc.) for using the software.

BRIEF DESCRIPTION OF THE DRAWINGS

The invention will be described and explained in greater detail below with reference to the example embodiments explained in the figures. In the figures FIG. 3 shows a second example embodiment of a personal dose report image, FIG. 4 shows a second example embodiment of an anonymized dose report image, FIG. 8 shows a second example embodiment of a determination unit.

DETAILED DESCRIPTION OF THE EXAMPLE EMBODIMENTS

Figure 1:
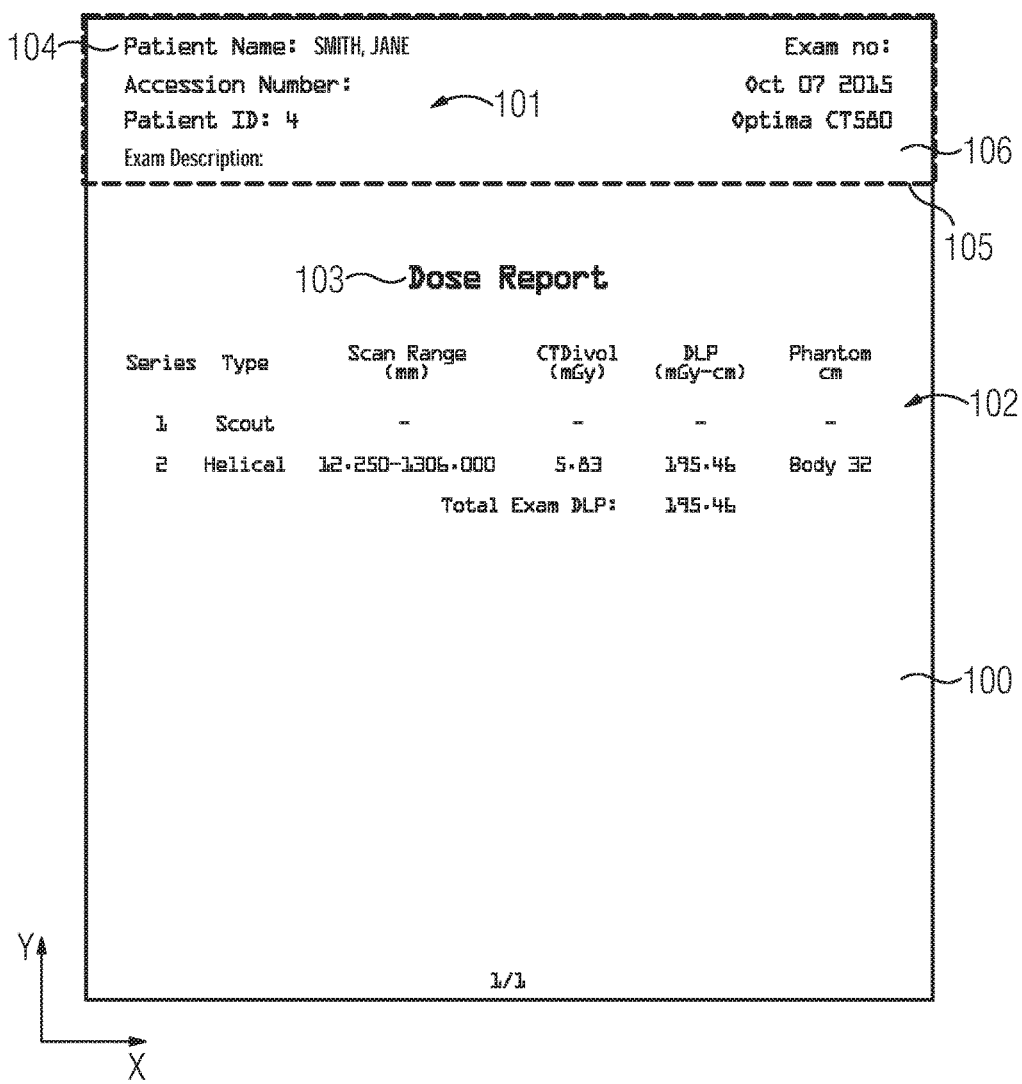
FIG. 1 shows a first example embodiment of a personal dose report image.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

At least one embodiment of the present invention is direct to a method for providing an anonymized dose report image. In at least one embodiment of the method, a personal dose report image is received via a first interface, wherein the personal dose report image comprises personal data and dose data of an imaging via ionizing radiation, wherein the personal data and the dose data is contained as rasterized text in the personal dose report image and wherein the personal data or the dose data includes a first signal word. Furthermore a first position of the first signal word in the personal dose report image is determined by optical character recognition via a first computing unit. Furthermore an image area in the personal dose report image is determined based on the first position via the first computing unit, wherein the image area comprises at least a part of the personal data. Furthermore an anonymized dose report image based on the personal dose report image is determined via the first computing unit, wherein at least the image area of the anonymized dose report image corresponding to the image area of the personal dose report image is anonymized. In particular the part of the personal data comprised by the image area, as well as the first signal word, can contain further personal data, in other words the part of the personal data comprised by the image area does not exclusively contain the first signal word.

The inventor has recognized that personal data and dose data in dose report images of different manufacturers is arranged in each case in contiguous, non-overlapping image areas. Through the anonymization of an entire image area based on the position of a signal word, and not just of individual datasets or of the signal word, the personal image data can thus be removed especially reliably.

By contrast with known methods, for embodiments of the inventive method it is not necessary to find all personal data via optical character recognition, but just individual signal words, which exhibit a far smaller variability than the totality of the personal data in the dose report image.

According to a further embodiment of the invention, a personal signal word is further sought in the anonymized dose report image by optical character recognition via a second computing unit. Here the second computing unit can in particular be identical to the first computing unit. Furthermore the anonymized dose report image is provided via a second interface if the personal signal word is not contained in the anonymized dose report image. Here the second interface can in particular be identical to the first interface. The personal signal word is advantageously not identical to the first signal word.

The inventor has recognized that an automatic search for a personal signal word enables it to be insured that there is no personal data present in the anonymized dose report image, without a dose report image having to be checked manually. Since the anonymized dose report image is only presented if the personal signal word is not found, it can thus be insured that no personal data is passed on to a third-party provider. These method steps in particular also make it possible to insure that no personal data is passed on, even if the format of the dose report image changes (for example by changes to the software or the hardware).

In particular it is thus possible by such a method to anonymize dose report images automatically and to make them available without personal data, in order for example to store them at a third-party provider in conformity with legislative regulations.

If the first computing unit and the second computing unit and also the first interface and the second interface are embodied separately and thus are not identical, then the first interface and the first computing unit (e.g. as a client computer) can in particular be spatially separated from the second interface and the second computing unit (e.g. in the cloud). This enables it to be insured in the cloud that no personal data is present in the anonymized dose report image, and therefore an unauthorized passing on of the personal data to a further service connected to the cloud is prevented. Furthermore it is also possible to prevent the uploading of further anonymized dose report images, in that for example a marker is set at the client, for example in the form of a flag, and thus not to incur any further costs for the uploading of dose report images not sufficiently anonymized.

Furthermore it is likewise possible to store the not sufficiently anonymized dose report images in a storage environment with restricted access rights, so that after a successful adaptation of the anonymization methods, the dose report images can be anonymized retroactively and are thus accessible to the statistical evaluation. An analogous method in relation to the extractability of data is described in the German patent with the file reference DE 10 2015 225 735.5, the entire contents of which are hereby incorporated herein by reference.

According to a further embodiment of the invention, the image area is arranged on precisely one side of a first straight line through the first position, wherein the first straight line is arranged parallel to a text direction of the personal data and/or of the dose data. In particular the image area can be delimited by the first straight line, furthermore the image area can comprise all pixels of the personal dose report image on precisely one side of the straight line. If the text direction is horizontal, then the image area is arranged in particular only above the first straight line or only below the first straight line. If the text direction is vertical, then the image area is arranged in particular only to the left or only to the right of the first straight line. The inventor has recognized that by a straight line through the first position, the personal data can be separated especially reliably from the dose data, and by a corresponding choice of the image area the anonymization is able to be carried out especially easily.

According to a further embodiment of the invention, a second position of a second signal word is furthermore determined, wherein the image area is arranged between the first straight line and a second straight line through the second position, wherein the second straight line is parallel to the first straight line. In particular the image area can be delimited both by the first straight line and also by the second straight line, furthermore the image area can comprise all pixels of the personal dose report image between the first straight line and the second straight line. Advantageously the second signal word is not identical to the first signal word. The inventor has recognized that by such a choice of the image area dose report images in which the dose data is arranged in two subareas, which are separated by personal data, can be anonymized especially well.

According to a further embodiment of the invention, the image area and the personal dose report image have the same extent in relation to a first coordinate axis. The first coordinate axis is in particular orthogonal to the first straight line and/or the second straight line, and thus in particular orthogonal to the text direction. The inventor has recognized that, independent of manufacturer, personal data is not arranged next to dose data in a dose report image with a horizontal text direction, and personal data is not arranged over or under dose data with a vertical text direction. Thus if the extent of the image area corresponds to the extent of the personal dose report image, personal data can be anonymized especially reliably, without dose data incorrectly being made unrecognizable.

According to a further embodiment of the invention, the image area is embodied as a rectangle. The inventor has recognized that personal data can be captured especially well by such a shape of image area.

According to a further embodiment of the invention, the image area comprises at least two subareas separate from one another. The inventor has recognized that, by such an image area, situations can be captured especially well in which the personal data is contained in a number of non-linked blocks in the personal dose report image.

According to a further possible embodiment of the invention, a third position of a third signal word and also a fourth position of a fourth signal word is furthermore determined by optical character recognition via the first computing unit. Furthermore a first subarea of the image area is arranged between the first and a third straight line, and a second subarea of the image area is arranged between the second and a fourth straight line, wherein the third straight line runs through the third position, and wherein the fourth straight line runs through the fourth position. Here the third straight line and/or the fourth straight line are in particular arranged parallel to the first straight line. Advantageously the third and the fourth signal word are neither identical to each other nor to the first or the second signal word. The inventor has recognized that, by an image area of this type, situations can be captured especially well in which the personal data is not contained in one block in the personal dose report image.

According to a further embodiment of the invention, the image area of the anonymized dose report image is anonymized such that none of the personal data is able to be extracted from the image area of the anonymized dose report image. In other words personal data is no longer received in the image area of the anonymized dose report image, in yet other words the image area of the anonymized dose report images is completely anonymized. In particular the image area of the anonymized dose report images is anonymized such that no personal data can be extracted via optical character recognition from the image area of the anonymized dose report image. In particular each pixel of the image area can be allocated an intensity value, which does not depend on the intensity values of the pixels of the image areas in the personal dose report image. The inventor has recognized that, by such an anonymization, the protection of the personal data can be insured especially reliably.

According to a further embodiment of the invention, in the anonymized dose report image, all pixels of the image areas of the anonymized dose report images are allocated a constant value or a random value. A constant value can in particular involve the value of the dose report images corresponding to the background color, in particular the maximum or the minimum value of a pixel. The random values can in particular be evenly distributed values. The inventor has recognized that, by such an anonymization, all information is removed from the image area, and thus the personal data can also be removed especially reliably.

According to a further embodiment of the invention, the personal signal word is a designation for a dataset of the personal data, and the first signal word is a designation for a dataset of the dose data or the personal data. In particular the second signal word, the third signal word and/or the fourth signal word is a designation for a dataset of the dose data or the personal data. A designation of a dataset can also be referred to here as the code, the code name or the name of the dataset. For example with the dataset "Name=John Smith" the designation of the dataset is "Name" (and the value of the dataset is "John Smith"), with dataset "Age: 65" the designation of the dataset is "Age" (and the value of the dataset is "65"). Since the personal dose report image must be read by a user, a corresponding designation is present for each dataset in the personal dose report image, since otherwise the value entered cannot generally be interpreted by the user. It is to be noted that a single designation can serve as the designation for a number of datasets, for example as the title of a table. The inventor has recognized that by the choice of a designation as signal word, unlike in the search for the value of a dataset, the variability is especially small, and therefore the position can be determined especially reliably.

According to a further embodiment of the invention, device information is also received during receipt, wherein the first signal word, the second signal word and/or the personal signal word are dependent on the device information. In particular a first signal word, a second signal word and/or the personal signal word can be assigned to an item of device information, in particular in the form of a code-value relationship. Here the device information in particular identifies the medical imaging device that has created the dose data image. The device information here can designate either the type of medical imaging device or the individual medical imaging device (as its serial number). The inventor has recognized that the designation of the dose data and/or the personal data in a dose report image is manufacturer-specific or device-specific. The choice of the signal word based on the device information for example therefore enables the personal data to be anonymized especially reliably.

At least one embodiment of the invention further relates to a determination unit for determining an anonymized dose report image, comprising:

First interface, embodied for receiving a personal dose report image,
wherein the personal dose report image comprises personal data and dose data of an imaging by way of ionizing radiation, wherein the personal data and the dose data are contained as rasterized text in the personal dose report image, and wherein the personal data or the dose data comprise a first signal word, First computing unit, embodied for first determination of a first position of the first signal word in the personal dose report image by optical character recognition,
further embodied for second determination of an image area in the personal dose report image based on the first position, wherein the image area comprises at least a part of the personal data,
further embodied for third determination of an anonymized dose report image based on the personal dose report image, wherein at least the image area of the anonymized dose report image corresponding to the image area of the personal dose report image is anonymized.

Such a determination unit can in particular be embodied to carry out the previously described inventive method and its embodiments. The determination unit is embodied to carry out this method and its embodiments, in that the first interface and the first computing unit are embodied to carry out the corresponding method steps. The determination unit can in particular also comprise a second computing unit and/or a second interface, in this case the second interface and the second computing unit are also embodied to carry out the corresponding method steps.

At least one embodiment of the invention also relates to a computer program product with a computer program as well as to a non-transitory computer-readable storage medium. A largely software-based realization has the advantage that determination units also used previously can be upgraded in a simple manner by a software update, in order to work in the inventive way. Such a computer program product, in addition to the computer program, can if necessary comprise additional elements such as e.g. documentation and/or additional components, as well as hardware components, such as e.g. hardware keys (dongles etc.) for using the software.

Ionizing radiation can in particular involve x-ray radiation. As an alternative it can also involve Alpha radiation, Beta radiation, Gamma radiation or neutron radiation. An imaging examination by way of ionizing radiation can in particular involve a fluoroscopy by way of x-ray radiation or a computed tomography imaging.

A personal or an anonymized dose report image is in particular a two-dimensional arrangement of pixels, to which in each case an intensity value is assigned. The term "picture element" is also known as a synonym for "pixel". The pixels can be arranged in particular on a rectangular or a square grid. The intensity values can in particular be represented by gray values, as an alternative the intensity values can also be shown by precisely two different colors, in particular by white or black.

A signal word is in particular given by a number of characters (letters and/or numbers), in particular by an individual word or by a group of words. A signal word is in particular the designation of a dataset. Synonyms for "designation" of the dataset here are "code", "code name" or "name" of the dataset.

A position of a signal word is given by at least one coordinate relating in each case to a coordinate axis. In particular the position of a signal word can also be given by a first coordinate relating to a first coordinate axis and by a second coordinate relating to a second coordinate axis. A position in a dose report image can in particular be given by precisely one pixel. The position of a signal word can in particular be determined based on a reference pixel of the signal word, in particular the position of the signal word can be determined by a shift in the coordinates of the reference pixel. The shift belonging to the first position can in particular depend on whether the dose data or the personal data comprise the first signal word, furthermore the shift belonging to the second position can depend on whether the dose data or the personal data comprise the second signal word. The first position of the first signal word does not necessarily have to be defined by one of the pixels of the first signal word or have to coincide with this, in precisely the same way the second position of the second signal word does not necessarily have to be defined by one of the pixels of the second signal word or have to coincide with this.

The extraction of text information from a raster graphic (such as e.g. an image with picture elements) is referred to as optical character recognition (OCR). "Text recognition" is also used as a synonym for "optical character recognition". In this process individual picture elements of the image can be grouped together, which are then mapped onto a letter, a number or character (which is represented by a number in a text encoding such as ASCII or Unicode). Optionally methods of context analysis can be used ("Intelligent Character Recognition", abbreviated to "ICR") in order to correct errors at word level or at sentence level, for example by comparison with a dictionary.

The way in which optical character recognition and context analysis function is known here to the person skilled in the art, therefore, for a more detailed description, the reader is referred to an article entitled "A survey of modern optical character recognition techniques" by Eugene Borovikov (https://arxiv.org/abs/1412.4183v1). Furthermore optical character recognition is provided by a plurality of program packages (in some cases available for free).

An image area of a personal dose report image or of an anonymized dose report image can be defined by a quantity of pixels of the personal dose report image or of an anonymized dose report image, wherein the quantity of pixels does not necessarily have to be contiguous. An image area can also be given by a surface in a personal dose report image or in an anonymized dose report image, in particular by a rectangle or by a square.

Two straight lines or a straight line and a coordinate axis are referred to as parallel when the respective direction vectors form an angle of less than 20° or more than 160°, in particular of less than 10° or more than 170°, in particular of less than 5° or more than 175°, in particular of less than 1° or more than 179°. In particular two straight lines or one straight line and a coordinate axis are referred to as parallel when the respective direction vectors form an angle of 0° or 180°. Here the angle between two direction vectors is the smallest angle between the vectors, in particular thus always less than or equal to 180°.

Two straight lines or a straight line and a coordinate axis are referred to as orthogonal when the respective direction vectors form an angle of between 70° and 110°, in particular between 80° and 100°, in particular between 85° and 95°, in particular between 89° and 91°. In particular two straight lines or one straight line and a coordinate axis are referred to as parallel when the respective direction vectors form an angle of 90°.

The primary text direction (a synonym is "direction of writing") of a text or a dataset refer in particular to the direction in which individual letters of a word or individual digits of a number are placed next to one another in accordance with their sequence, in order to form the respective word or the respective number. The primary text direction with a Latin font is referred to as horizontal and running to the right (i.e. written from left to right), the text direction in Chinese is referred to as vertical. The use of "text direction" without an identifying adjective is always to be understood as a synonym for "primary text direction".

The secondary text direction of a text or of a dataset refers in particular to the direction in which individual lines of a text are arranged next to one another in accordance with their sequence, in order to form the respective text. The secondary text direction with a Latin font is referred to as vertical or as "top to bottom". As a rule the secondary text direction is arranged orthogonal to the primary text direction.

Figure 2:
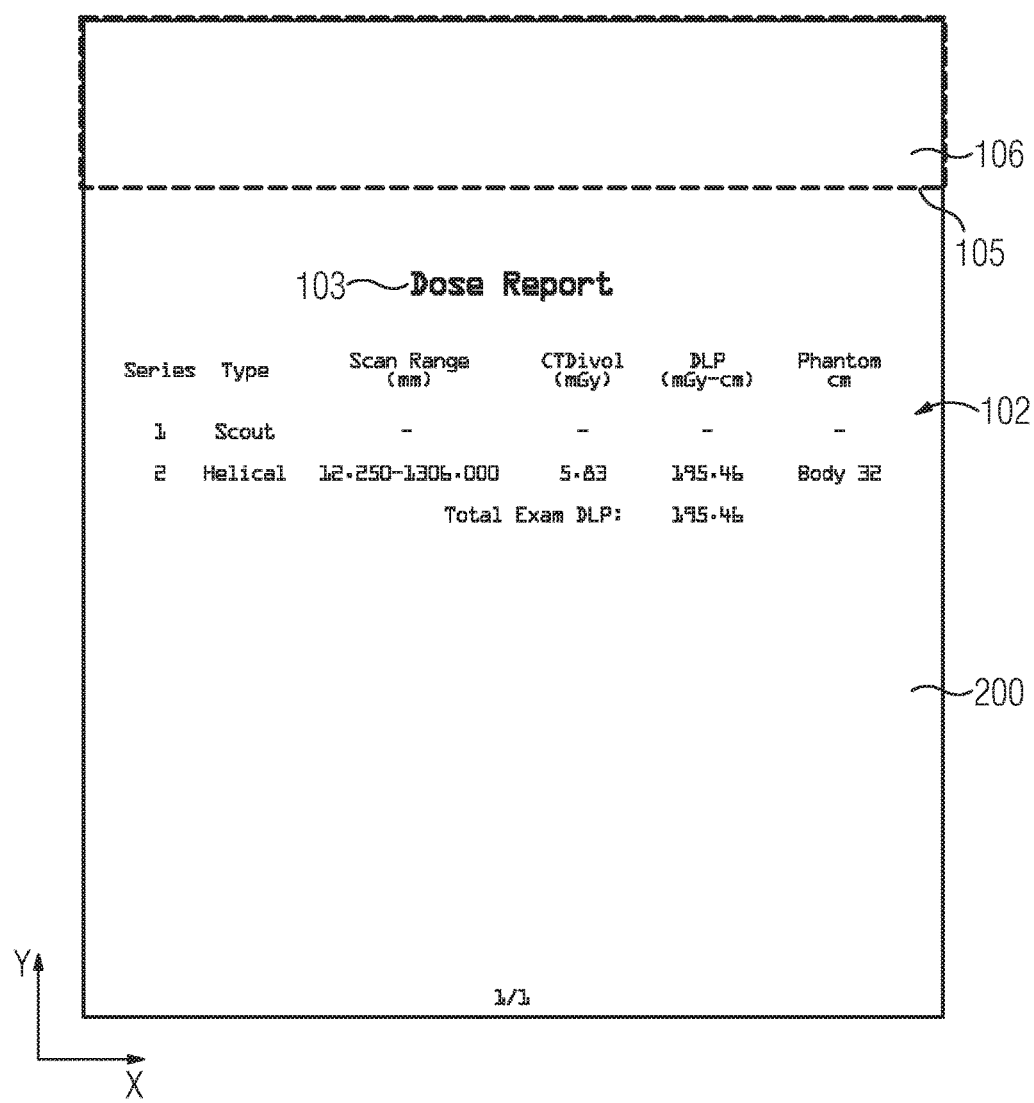
FIG. 2 shows a first example embodiment of an anonymized dose report image.

FIG. 1 shows a first example embodiment of a personal dose report image 100, FIG. 2 shows the first example embodiment of an anonymized dose report image 200 determined by the inventive method.

The personal dose report image 100 comprises personal data 101 and dose data 102, wherein both the personal data 101 and the dose data 102 are contained as rasterized text in the personal dose report image 100, in particular in the intensity values of the pixels of the personal dose report image 100. The text direction of both the personal data 101 and also of the dose data 102 is horizontal in the example embodiment shown, in other words embodied in parallel to the first coordinate axis X. As an alternative personal dose report images 100 with one or more other text directions can naturally also be received.

In the example embodiment shown the first signal word 103 is the word group "Dose Report". The first position 504 of the first signal word 103 is given here by a coordinate relating to a second coordinate axis Y, in particular the first position 504 is the coordinate of the picture element in the upper left corner of the first letter "D" of the first signal word 103, shifted by a constant value. Based on the first position 504 of the first signal word 103, a first straight line 105 can be determined, which, in the example embodiment shown, is arranged parallel to the first coordinate axis X and runs through the first position 504 of the first signal word 103. In other words all points of the first straight line 105, in relation to the second coordinate axis Y, have the same coordinate as the first position 504 of the first signal word 103.

In the example embodiment shown the image area 106 is then given by those pixels of the personal dose report image 100, which are arranged above the first straight line 105. In other words the image area 106 is given by those pixels of the personal dose report image 100, which, in relation to the second coordinate axis Y, have a larger coordinate than the first position 504, in particular the image area 106 is thus delimited by the first straight line 105.

The anonymized dose report image 200 corresponds in this example embodiment to the personal dose report image 100, wherein the intensity values of all pixels of the image area 206 in the anonymized dose report image 200 (which in its position and in its extent corresponds to the image area 106 in the personal dose report image 100) have been occupied by a constant value. In this example embodiment the constant value corresponds to the background color "white".

In the example embodiment shown, the personal signal word 104 is "Patient Name". The personal signal word 104, just like the personal data 101, is not contained in the anonymized dose report image 200.

FIG. 3 shows a second example embodiment of a personal dose report image 300, FIG. 4 shows the associated second example embodiment of an anonymized dose report image 400 determined by the inventive method.

The personal dose report image 300 comprises personal data 301 and dose data 302, wherein both the personal data 301 and the dose data 302 is contained as rasterized text in the personal dose report image 300, in particular in the intensity values of the pixels of the personal dose report image 300. The text direction of both the personal data 301 and also of the dose data 302 is horizontal in the example embodiment shown, in other words embodied parallel to the first coordinate axis X. As an alternative personal dose report images 300 with one or more other text directions can naturally also be received.

In the example embodiment shown, the first signal word 303.1 is the word group "Patient ID", the second signal word 303.2 is the word "Xposure". The first position 504 of the first signal word 303.1 as well as the second position of the second signal word 303.2 are given here by a coordinate relating to a second coordinate axis Y, in particular the first position 504 is the coordinate of the picture element in the upper left corner of the first letter "P" of the first signal word 303.1, shifted by a constant, and the second position is the coordinate of the picture element in the upper left corner of the first letter "X" of the second signal word 303.2, shifted by a constant. Based on the first position 504 of the first signal word 303.1, a first straight line 305.1 can be determined, which in the example embodiment shown, is arranged parallel to the first coordinate axis X and runs through the first position 504 of the first signal word 303.1. In other words all points of the first straight line 305.1, in relation to the second coordinate axis Y, have the same coordinate as the first position 504 of the first signal word 303.1. Furthermore, based on the second position of the second signal word 303.2, a second straight line 305.2 can be determined, which, in the example embodiment shown, is arranged parallel to the first coordinate axis Y and runs through the second position of the second signal word 303.2. In other words all points of the second straight line 305.2, in relation to the second coordinate axis Y, have the same coordinate as the second position of the second signal word 303.2.

In the example embodiment shown, the image area 306 is then given by those pixels of the personal dose report image 300, which are arranged below the first straight line 305.1 and at the same time above the second straight line 305.2. In other words the image area 306 is given by those pixels of the personal dose report image 300, which, in relation to the second coordinate axis Y, have a smaller coordinate than the first position 504 and at the same time have a larger coordinate than the second position. The image area 306 is thus in particular delimited by the first straight line 305.1 and the second straight line 305.2.

The anonymized dose report image 400 corresponds in this example embodiment to the personal dose report image 300, wherein the intensity values of all pixels of the image area 406 in the anonymized dose report image 400 (which corresponds in its position and in its extent to the image area 306 in the personal dose report image 300) have been occupied with a constant value. In this example embodiment the constant value corresponds to the background color "white".

In the example embodiment shown, the personal signal word 304 is "Age". The personal signal word 304, just like the personal data 301, is not contained in the anonymized dose report image 400.

As an alternative to the example embodiments shown, the image area 106, 306 of the personal dose report image 100, 300 (and thus also the image area 206, 406 of the anonymized dose report image) can each comprise a number of subareas. These subareas can likewise be determined via signal words.

Figure 5:
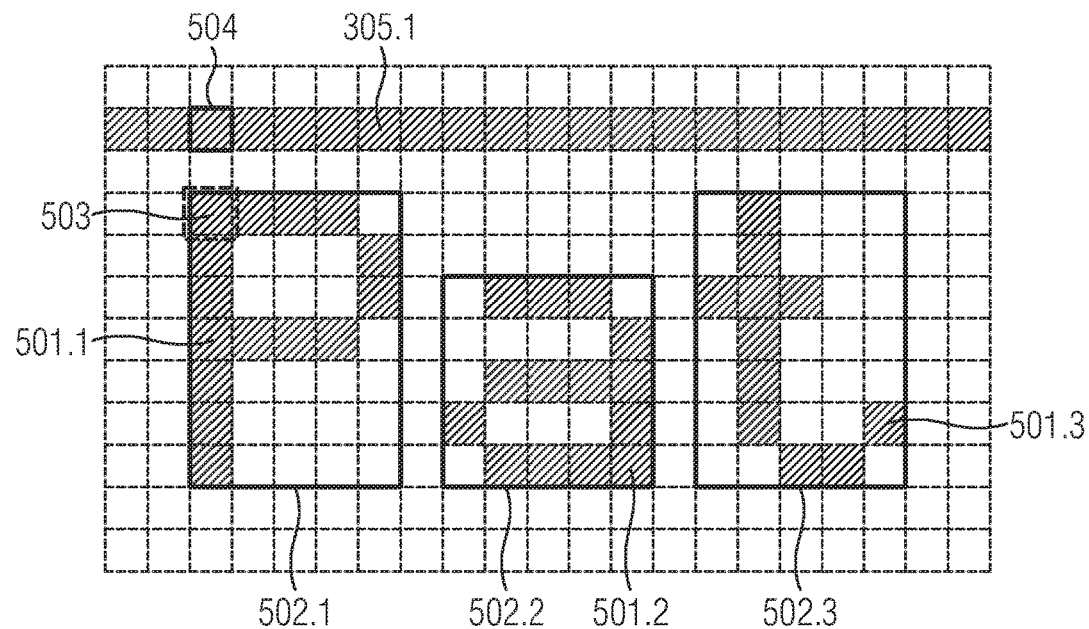
FIG. 5 shows the position of a signal word.

FIG. 5 shows a first position 504 of a first signal word 103, 303.1, the explanations for FIG. 5 can however also be transferred to the second position of a second signal word 303.2.

Shown in FIG. 5 are rasterized letters 501.1, 501.2, 501.3 of the first signal word 103, 303.1. Here the pixels of the letters 501.1, 501.2, 501.3 of the first signal word 103, 303.1 have an intensity differing from the background intensity or a gray value differing from the background gray value. Known algorithms of optical character recognition assign any amount of pixels, which can be recognized as belonging to a single letter, to a letter area 502.1, 502.2, 502.3. The actual recognition of a letter 501.1, 501.2, 501.3 takes place within this letter area 502.1, 502.2, 502.3.

The first position 504 is based on a reference pixel 503 assigned to the first letter 502.1 of the first signal word 103, 303.1. The reference pixel 503 is that pixel of the first letter 501.3, which has a minimum coordinate in relation to the first coordinate axis X, and which has a maximum coordinate in relation to the second coordinate axis Y. In other words the reference pixel 503 is that pixel at the upper left, when the horizontal of the personal dose report image 100, 300 coincides with the text direction.

In the example embodiment shown, the first position 504 is given by a pixel that originates from the reference pixel 503 through a shift by two pixels in the positive direction of the second coordinate axis Y. As an alternative it is naturally also possible to choose another reference pixel and/or another shift. The reference pixel and/or the shift can in particular also be based on device information, furthermore the reference pixel or the shift can also depend on whether the first signal word 103, 303.1 is person-related or dose-related.

Furthermore the first straight line 305.1 is shown in FIG. 5, which is embodied parallel to the first coordinate axis X as well as parallel to the text direction and also runs through the first position 504.

Figure 6:
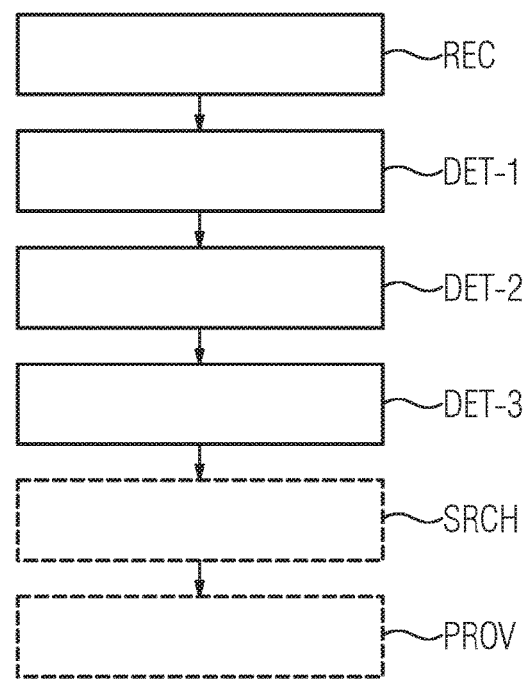
FIG. 6 shows a flow diagram of an example embodiment of the method.

FIG. 6 shows a flow diagram of an example embodiment of the method for determining an anonymized dose report image 200, 400.

The first step of the example embodiment shown is the receiving REC of a personal dose report image 100, 300 via a first interface 701, 801.1, wherein the personal dose report image 100, 300 comprises personal data 101, 301 and dose data 102, 302 of an imaging by way of ionizing radiation, wherein the personal data 101, 301 and the dose data 102, 302 is contained as rasterized text in the personal dose report image, and wherein the personal data 101, 301 or the dose data 102, 302 comprise a first signal word 103, 303.1.

In the example embodiment shown the ionizing radiation is x-ray radiation, and the imaging is a computed tomography imaging. The personal dose report image 100, 300 comprises a quantity of pixels (here 512 times 512 pixels, but other image formats are also possible as an alternative), to each of which an intensity value is assigned. In this example embodiment the intensity value can contain precisely two values ("0" or "1"), wherein the value "0" in the personal dose report image 100, 300 is shown in black, and wherein the value "1" in the personal dose report image 100, 300 is shown in white. In this case the background is shown in white, and the rasterized text is shown in black. As an alternative it is also possible for the background to be shown in black, and for the rasterized text to be shown in white. As an alternative gray values or color values are naturally also possible.

The personal data 101, 301 and the dose data 102, 302 are contained in the personal dose report image 100, 300 in such a way that both the personal data 101, 301 and also the dose data 102, 302 are present in text form. The text is contained in a rasterized form in the personal dose report image 100, 300, i.e. the intensity values of the pixels represent the text graphically and readably for a user.

Personal data 101, 301, in the example embodiment shown, comprises the name, the sex and the age of the patient examined via computed tomography. Dose data 102, 302 comprises for example a CTDI ("Computed Tomography Dose Index") or the DLP ("Dose Length Product"), alternatively also the current or the voltage of the x-ray tube, or other parameters that can be included for evaluation of the radiation dose absorbed by the patient during the examination.

It goes without saying that the personal data 101, 301 and the dose data 102, 302 can also comprise further parameters not explicitly described here.

In the example embodiment shown, the personal data 101, 301 and/or the dose data 102, 302 comprise both the designation of a dataset and also the actual value of the dataset. For example the personal data 101, 301 comprises as the dataset the name of the patient, this comprises a designation ("Name:") and a value ("John Smith"). The dose data 102, 302 comprises for example the CTDI of the imaging examination, this comprises a designation ("CTDI:") and a value ("10.0 mGy"). The position of the designation can vary here, for example the designation can be located directly at the respective value, or as a title in a table as the designation of a number of values.

Advantageously, in the example embodiment shown, device information can also be received during receiving REC. Here, in this example embodiment, this involves the manufacturer as well as the type designation of the medical imaging device that has created the personal dose report image.

The next step of the example embodiment shown is the first determination DET-1 of a first position 504 of the first signal word 103, 303.1 in the personal dose report image 100, 300 through optical character recognition via a first computing unit 702, 802.1.

In the personal dose report image 100 the first signal word 103 is the word group "Dose Report", in the personal dose report image 300 the first signal word 303.1 is the word group "Patient ID". In an alternate form of embodiment the second position of a second signal word 303.2 is further determined. The second signal word in the personal dose report image 300 is the word "Xposure".

The first signal word and the optional second signal word, in the example embodiment shown, are retrieved on the basis of the device information from a database 706. In the example embodiment shown, the device information comprises a type designation of the medical imaging device, a version number of the medical imaging device and also the output language of the medical imaging device, wherein the medical imaging device has created the personal dose report image 100, 300.

As an alternative to retrieval from a database, it is also possible to use a permanently specified first signal word. As an alternative a list of pre-specified signal words can also be specified, which are processed in a given order, and the signal word of the list, which can be found as the first in the personal dose report image 100, 300 through optical character recognition, is used as the first signal word.

In the example embodiment shown, the first position 504 is based on the two-dimensional coordinates of a reference pixel 503 of the first character ("D" or "P" respectively) of the first signal word 103, 303.1, furthermore the second position is based on the two-dimensional coordinates of a reference pixel 503 of the first character ("X") of the second signal word 303.2. In particular the first position 504 and the second position is produced from the shift of the respective reference pixel 504 in the direction of the positive second coordinate axis Y by a pre-specified value, for example by two pixels. The shift value can optionally likewise be stored in a database 706.

The program "Tesseract" is used for optical character recognition in this example embodiment. Naturally the use of another algorithm and/or of other software is also always possible, known alternatives are for example the programs "Fine Reader" from ABBYY or "Acrobat Text Capture" from Adobe.

The next step of the example embodiment shown is the second determination DET-2 of an image area 106, 306 in the personal dose report image 100, 300, based on the first position 504, via the first computing unit 702, 802.1, wherein the image area 106, 306 comprises at least a part of the personal data 101, 301. In the example embodiment shown, the image area 106, 306 and the personal dose report image 100, 300 have the same extent in relation to the first coordinate axis X, as an alternative other sizes of the image area 106, 306 are naturally also conceivable.

Here a first straight line 105, 305.1 is determined, wherein the first straight line 105, 305.1 runs through the first position 504 and is arranged parallel to the text direction of the personal data 101, 301. Optionally a second straight line 305.2 can also be determined, which is parallel to the first straight line 305.1 and runs through the second position.

For the personal dose report image 100 the image area 106 is arranged on precisely one side in relation to the first straight line 105. In particular the image area 106 comprises all pixels of the personal dose report image 100, which, in relation to the second coordinate axis Y, have a larger coordinate than the first position 504, in particular the first straight line 105 delimits the image area 106.

For the personal dose report image 300 the image area 306 is arranged between the first straight line 305.1 and the second straight line 305.2. In particular the image area 306 comprises all pixels of the personal dose report image 300, which, in relation to the second coordinate axis Y, have a larger coordinate than the second position and have a smaller coordinate than the first position 504, in particular the first straight line 305.1 and the second straight line 305.2 thus delimit the image area 306.

The location of the image area 106, 306 in relation to the first position 504 and the optional second position or in relation to the first straight line 105, 305.1 and the optional second straight line 305.2, can likewise be stored in the database 706 and be retrieved on the basis of the device information from the database 706.

The next step of the method is the third determination DET-3 of an anonymized dose report image 200, 400, based on the personal dose report image 100, 300, via the first computing unit 702, 802.1, wherein at least the image area 206, 406 of the anonymized dose report images 200, 400 corresponding to the image area 106, 306 of the personal dose report image 100, 300 is anonymized.

In the example embodiment shown, the anonymized dose report image 200, 400 has the same number and the same arrangement of pixels as the personal dose report image 100, 300. Furthermore the intensity values of the pixels of the anonymized dose report image 200, 400 outside of the image areas 206, 406 match the intensity values of the pixels of the personal dose report image 100, 300 pixel-by-pixel.

Furthermore, in the example embodiment shown, in the anonymized dose report image 200, 400, each pixel in the image area 306 is allocated a constant value, this corresponds in particular to a value assigned to the background. As an alternative, each pixel in the image area 206, 406 can also be allocated a random value. As an alternative, each pixel in the image area 206, 406, can also be allocated a value, which does not depend on the values of the pixels in the image area 206, 406 in the personal dose report image 100, 300.

In the example embodiment shown, as optional next steps of the method, there are a search SRCH for a personal signal word 104, 304 in the anonymized dose report image 200, 400 through optical character recognition via the second computing unit 702, 802.2 as well as a provision PROV of the anonymized dose report images 200, 400 via the second interface 701, 802.2, if the personal signal word 104, 304 is not contained in the anonymized dose report image 200, 400 (the personal signal word 104, 304, in example embodiments of FIG. 2 and FIG. 4 shown, is not contained in the anonymized dose report image 200, 400, these are thus provided). In the example embodiment shown, the first computing unit 702, 802.1 is identical to the second computing unit 702, 802.2, likewise the first interface 701, 801.1 is identical to the second interface 701, 801.2. As an alternative the first computing unit 702, 802.1 can be not identical to the second computing unit 702, 802.2 and/or the first interface 701, 801.1 can be not identical to the second interface 701, 801.2.

As an alternative a number of personal signal words can always be sought during the search SRCH, the provision PROV of the anonymized dose report images 200, 400 occurs when none of the personal signal words is contained in the anonymized dose report image 200, 400. When a number of personal signal words are sought, this search can in particular be parallelized, i.e. various of the personal signal words can be sought on different parts of the second computing unit 702, 802.2.

The personal signal word 104, 304 or the plurality thereof, in the example embodiment shown, is not dependent on the device information, but is permanently specified. In particular the signal words "Patient", "Name", "Age" and/or "Sex" or their translation into another language can be involved. As an alternative it is also possible for the personal signal word 104, 304 to depend on the device information.

Figure 7:
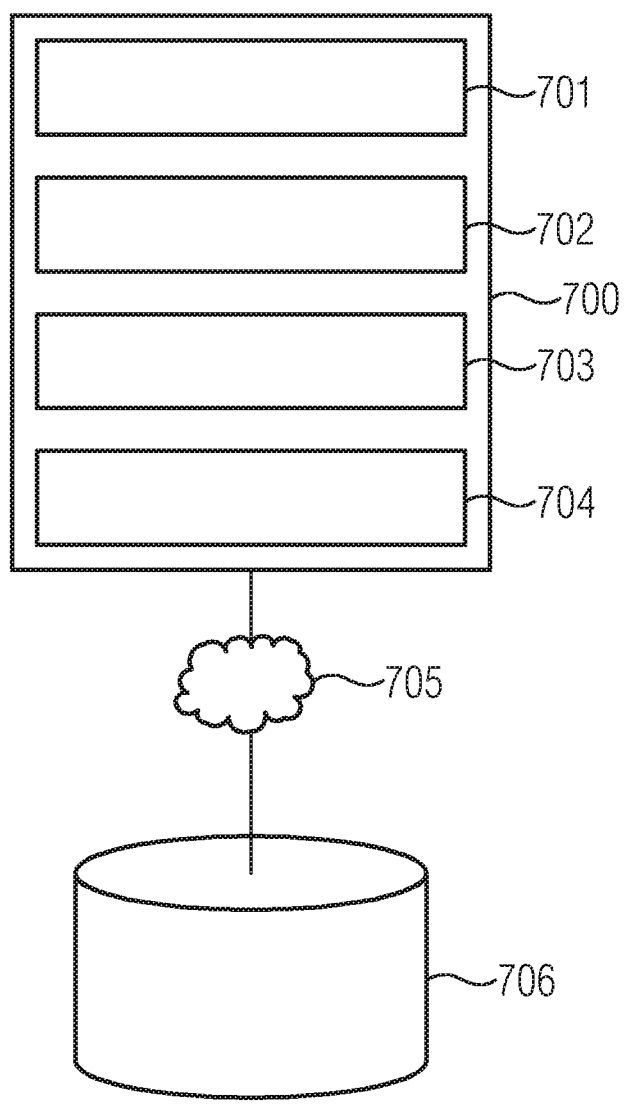
FIG. 7 shows a first example embodiment of a determination unit.

FIG. 7 shows a first example embodiment of a determination unit 700 for determining an anonymized dose report image 200, 400. The determination unit 700 shown here is designed to carry out an embodiment of the inventive method. This determination unit 700 comprises a first and second interface 701, a first and second computing unit 702, an optional first memory unit 703 and also an optional first input and output unit 704. Here the first and the second interface 701 are embodied identical or integrated into one another, furthermore the first and the second computing unit 702 are embodied identical integrated into one another.

FIG. 8 shows a second example embodiment of a determination unit 800 for determining an anonymized dose report image 200, 400. The determination unit 800 shown here is designed to carry out an embodiment of the inventive method. This determination unit 800 comprises a first sub-determination unit 800.1 and a second sub-determination unit 800.2, which are connected via a network 805. The network 805 is however not necessarily to be understood as part of the determination unit 800. The first sub-determination unit 800.1 comprises a first interface 801.1, a first computing unit 802.1, an optional first memory unit 803.1 as well as an optional first input and output unit 804.1. The second sub-determination unit 800.2 comprises a second interface 801.2, a second computing unit 802.2, an optional second memory unit 803.2 and also an optional second 804.2.

The determination unit 700, the first sub-determination unit 800.1 and/or the second sub-determination unit 800.2 can in particular involve a computer, a microcontroller or an integrated circuit. As an alternative the determination unit 700, the first sub-determination unit 800.1 and/or the second sub-determination unit 800.2 can involve a real or virtual network of computers (a technical term for a real network is a cluster, a technical term for a virtual network is a cloud). A first interface 701, 801.1 and/or a second interface 701, 801.2 can involve a hardware or software interface (for example PCI bus, USB or Firewire). A first interface 701, 801.1 and/or a second interface 701, 801.2 can in particular also comprise individual part interfaces, in particular an input interface and/or an output interface. A first computing unit 702, 802.1 and/or a second computing unit 702, 802.2 can have hardware elements or software elements, for example a microprocessor or an FPGA (Field Programmable Gate Array). A first memory unit 703, 803.1 and/or a second memory unit 803.2 can be realized as Random Access Memory, abbreviated to RAM) or as permanent mass storage (hard disk, USB stick, SD card, Solid State Disk). A first input and output unit 704, 804.1 and/or a second input and output unit 804.2 comprises at least one input unit and/or at least one output unit.

In the example embodiments shown the determination unit 700 or the first sub-determination unit 800.1 and the second sub-determination unit 800.2 respectively are connected via a network 705, 805 to a database 706, 806. A network 705, 805 can involve a wired network (for example Ethernet or USB) or a wireless network (for example via Bluetooth or a wireless network such as a Wireless LAN). The network 705, 805 can also involve an intranet or the Internet. The database 706, 806, in the example shown, is embodied separately from the determination unit 700, 800 in a database server, as an alternative the database 706, 806 can also be embodied in the first memory unit 703, 803.1 and/or the second memory unit 803.2 of the determination unit 700, 800. The connection of the determination unit 700, 800 to the database 706, 806 is optional. It is also possible in the second example embodiment for both the first sub-determination unit 800.1 and also the second sub-determination unit 800.2 to be connected to a separate database via a separate network, and for these separate networks not to be identical 805 to the connection of the first sub-determination unit 800.1 and the second sub-determination unit 800.2.

The database 706, 806, in the example embodiments shown, comprises assignments between device information of medical imaging devices and information for carrying out the inventive method. Here the device information can comprise in particular the manufacturer, the type designation and/or a serial number of the medical imaging device. Information for carrying out embodiments of the inventive method can comprise one or more of the following items of information:

First signal word 103.1, 303.1, second signal word 303.2 and/or personal signal word 104, 304

Dependence of the first position 504 on the position of the pixels of the first signal word 103.1, 303.1 and/or dependence of the second position on the position of the pixels of the second signal word 303.2

Location and extent of the image areas 106, 306 relative to the first position 504 and/or relative to the second position.

However this information does not necessarily have to be stored in the database 706, 806, but can for example also be pre-specified as a fixed value in a program code.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for determining an anonymized dose report image, comprising:
    receiving a personal dose report image via a first interface, the personal dose report image including personal data and dose data of an imaging by way of ionizing radiation, the personal data and the dose data being contained as rasterized text in the personal dose report image and the personal data or the dose data including a first signal word;
    first determining, via a first computing unit, a first position of the first signal word in the personal dose report image through optical character recognition;
    second determining, via the first computing unit, an image area in the personal dose report image based on the first position determined, the image area including at least a part of the personal data; and
    third determining, via the first computing unit, an anonymized dose report image based on the personal dose report image, at least the image area of the anonymized dose report image, corresponding to the image area of the personal dose report image, being anonymized, wherein, to all pixels of the image area of the anonymized dose report image, a constant value, a random value or a value which does not depend on intensity values of the pixels of the image area of the personal dose report image, is allocated.

2. The method of claim 1, further comprising:
    searching, via a second computing unit, for a personal signal word in the anonymized dose report image, through optical character recognition; and
    provisioning the anonymized dose report image, via a second interface, upon the personal signal word not being contained in the anonymized dose report image.

3. The method of claim 2, wherein the image area is arranged on precisely one side of a first straight line through the first position, and wherein the first straight line is arranged in parallel to a text direction of at least one of the personal data and the dose data.

4. The method of claim 3, wherein the image area and the personal dose report image include a same extent along a first coordinate axis.

5. The method of claim 3, wherein during the first determining, a second position of a second signal word is further determined,
    wherein the image area is arranged between the first straight line and a second straight line through the second position, and
    wherein the second straight line is parallel to the first straight line.

6. The method of claim 5, wherein the receiving includes receiving device information, and wherein at least one of the first signal word, the second signal word and the personal signal word is dependent on the device information.

7. The method of claim 5, wherein the image area and the personal dose report image include a same extent along a first coordinate axis.

8. The method of claim 1, wherein the image area is embodied as a rectangle.

9. The method of claim 1, wherein the image area includes at least two subareas, separated from one another.

10. The method of claim 1, wherein at least one of
    the personal signal word is a designation for a dataset of the personal data and
    the first signal word is a designation for a dataset of the dose data or the personal data.

11. A non-transitory computer program product, directly loadable into a memory of a processor, including program sections for carrying out the method of claim 1 when the program sections are executed by the processor.

12. A non-transitory computer-readable storage medium, storing program sections readable and executable by a processor, to execute the method of claim 1 when the program sections are executed by the processor.

13. The method of claim 1, wherein the image area is arranged on precisely one side of a first straight line through the first position, and wherein the first straight line is arranged in parallel to a text direction of at least one of the personal data and the dose data.

14. The method of claim 13, wherein during the first determining, a second position of a second signal word is further determined,
    wherein the image area is arranged between the first straight line and a second straight line through the second position, and
    wherein the second straight line is parallel to the first straight line.

15. The method of claim 1, wherein the receiving includes receiving device information, and wherein the first signal word is dependent on the device information.

16. A determination unit for determining an anonymized dose report image, comprising:

a first interface, embodied to receive a personal dose report image, the personal dose report image including personal data and dose data of an imaging by way of ionizing radiation, the personal data and the dose data being contained as rasterized text in the personal dose report image, and the personal data or the dose data (including a first signal word;

a first computing unit, embodied for
- a first determination of a first position of the first signal word in the personal dose report image through optical character recognition,
- a second determination of an image area in the personal dose report image based on the first position, the image area including at least a part of the personal data, and
- a third determination of an anonymized dose report image based on the personal dose report image, at least the image area of the anonymized dose report image, corresponding to the image area of the personal dose report image, being anonymized, wherein, to all pixels of the image area of the anonymized dose report image, a constant value, a random value or a value which does not depend on intensity values of the pixels of the image area of the personal dose report image, is allocated.

17. The determination unit of claim 16, wherein the first computing unit includes a processor.

* * * * *